(12) United States Patent
Namiki (10) Patent No.: US 7,728,980 B2
(45) Date of Patent: Jun. 1, 2010

(54) OPTICAL UNIT

(75) Inventor: Mitsuru Namiki, Hannou (JP)

(73) Assignee: Olympus Corporation, Tokyo (JP)

( * ) Notice: Subject to any disclaimer, the term of this patent is extended or adjusted under 35 U.S.C. 154(b) by 18 days.

(21) Appl. No.: 12/313,309

(22) Filed: Nov. 18, 2008

(65) Prior Publication Data

US 2009/0128804 A1    May 21, 2009

(30) Foreign Application Priority Data

Nov. 20, 2007   (JP) .............................. 2007-300829

(51) Int. Cl.
*G01N 21/55* (2006.01)
(52) U.S. Cl. ...................... 356/445; 356/136
(58) Field of Classification Search ......... 356/445–448, 356/128–137; 359/385, 387
See application file for complete search history.

(56) References Cited

U.S. PATENT DOCUMENTS 5,440,126 A * 8/1995 Kemsley ................ 250/339.12

2002/0060791 A1 * 5/2002 Stumbo et al. .............. 356/317
2002/0171841 A1 * 11/2002 Elkind et al. ................ 356/445
2003/0107741 A1 * 6/2003 Pyo et al. .................... 356/445

FOREIGN PATENT DOCUMENTS

JP         2005-337940         12/2005

* cited by examiner

*Primary Examiner*—Hoa Q Pham
(74) *Attorney, Agent, or Firm*—Kenyon & Kenyon LLP (57) ABSTRACT

An optical unit includes a light source unit emitting parallel light; a light-receiving element array; and a prism rendering emitted light from the light source unit incident on a specimen placement section and introducing totally reflected light from the specimen placement section into the light-receiving element array. The prism has an entrance surface rendering the parallel light emitted from the light source unit incident on the prism, a curved reflecting surface which reflects light passing through the entrance surface and incident on the prism toward a focal position thereof, the specimen placement section of a planar shape provided at a position including the focal position of the curved reflecting surface, and an exit surface making light totally reflected at the focal position of the curved reflecting surface in the specimen placement section emerge into the outside of the prism.

5 Claims, 6 Drawing Sheets

OPTICAL UNIT

This application claims benefits of Japanese Patent Application No. 2007-300829 filed in Japan on Nov. 20, 2007, the contents of which are incorporated herein by reference.

BACKGROUND OF THE INVENTION

1. Field of the Invention

This invention relates to an optical unit used in a specimen analysis for the quantitative analysis of a specimen or a substance in the specimen such as a refractive index or an immunity measured value.

2. Description of Related Art

As a conventional specimen analyzer, there is the device that light of incident angles in a preset range including the angle of total reflection (hereinafter referred to as the preset convergent light) is rendered incident on a specimen placement section and the intensity of reflected light from the specimen placement section corresponding to each of the incident angles is detected so that an incident angle where the detected intensity is abruptly changed is detected.

For such a specimen analyzer, a device that, for example, the difference of the refractive index between substances is used to make an analysis is available. In this specimen analyzer, a specimen to be examined is placed at the specimen placement section consisting of a substance with a known refractive index. The preset convergent light is then rendered incident on the surface of the specimen placement section. At this time, light incident at an angle smaller than a critical angle ceases to undergo total reflection at the surface of the specimen placement section. By detecting the incident angle in this case, the refractive index of the specimen to be examined is determined and the physical properties of the specimen to be examined can be analyzed.

Also, for example, in a specimen analyzer utilizing the occurrence of surface plasmon, the specimen placement section is provided with a metal film on its surface. The specimen to be examined is placed on the metal film of the specimen placement section and the preset convergent light is rendered incident on the surface of the metal film. Here, when the light is incident at angles exceeding the critical angle, an evanescent wave having electric field distribution is produced at an interface between the metal film and the specimen to be examined. The surface plasmon is excited on the metal film by the evanescent wave. In addition, with respect to light incident at a particular incident angle, of light incident at the angles exceeding the critical angle, the evanescent wave and the surface plasmon cause wave number matching to bring about a resonance state. In this resonance state, the energy of light is transferred to the surface plasmon. As a result, in the light incident at the particular incident angle, the intensity of reflected light is rapidly decreased. Thus, by detecting the incident angle where the intensity of the reflected light is rapidly decreased, the wave number of the surface plasmon is determined and the physical properties of the specimen to be examined can be analyzed.

As the specimen analyzer utilizing the occurrence of the surface plasmon, a device set forth in Japanese Patent Kokai No. 2005-337940 is disclosed.

Figure 1:
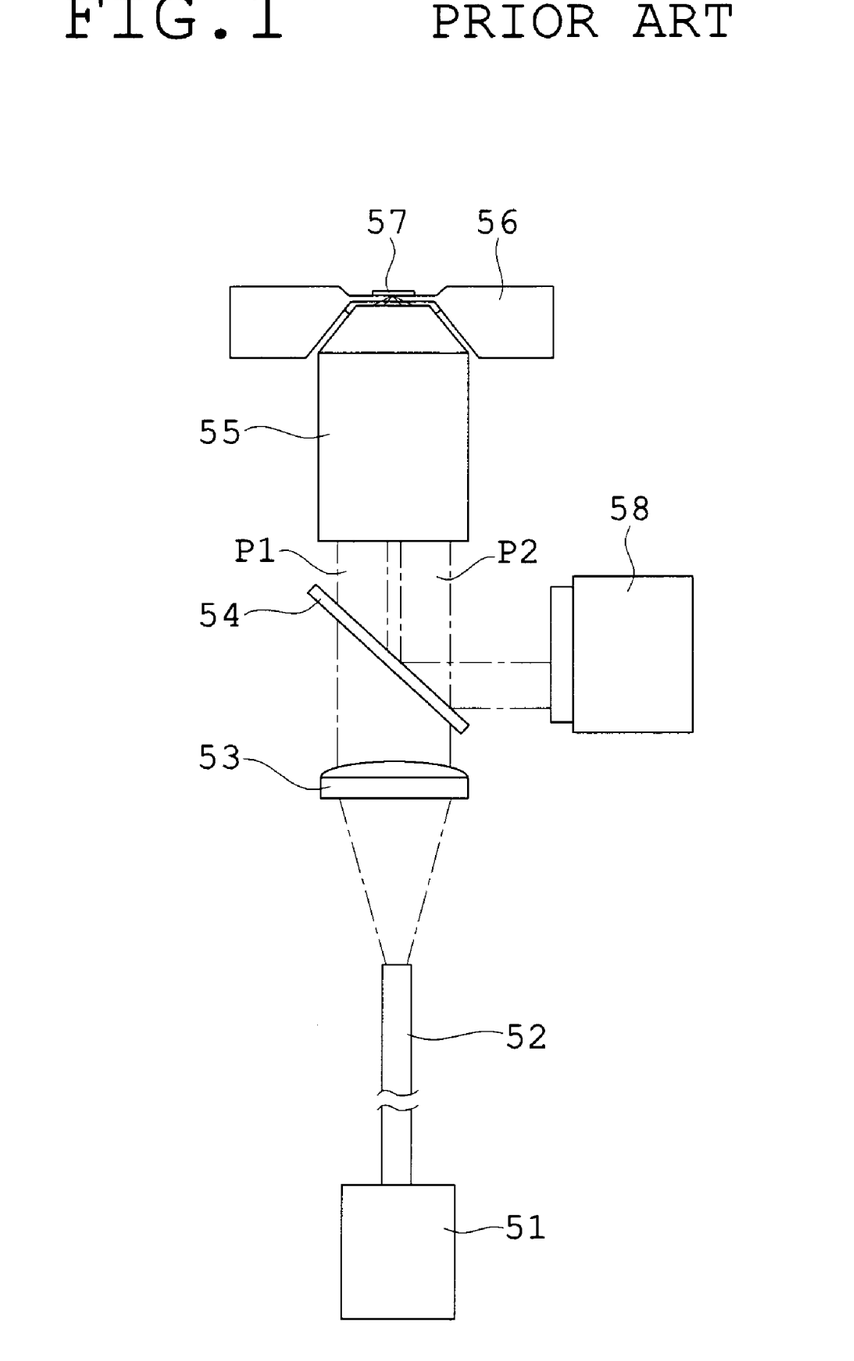
FIG. 1 is a view showing a schematic structure of one example of a conventional specimen analyzer.

The specimen analyzer of Kokai No. 2005-337940, as shown in FIG. 1, is constructed with a light source section, a lens 55, a transparent substrate 56, and a photodetector 58. The light source section has a laser light irradiating device 51, an optical fiber 52, a collimation lens 53, and a strip-shaped aperture (not shown) provided to a mirror 54. In Kokai No. 2005-337940, parallel light P1 from the light source section is converted into convergent light through the lens 55. On the opposite surface of the transparent substrate 56 on which a specimen (not shown) is placed, a metal film 57 is deposited. The surface of the metal film 57 is irradiated with the convergent light. Totally reflected light is collected through the lens 55. The collected light is converted into parallel light P2 that travels in a direction opposite to that of the parallel light from the light source section and is detected by the photodetector 58.

In the conventional specimen analyzer, like that of Kokai No. 2005-337940, the parallel light from the light source section has been converted into convergent light through the lens when an examination position is irradiated with the light.

SUMMARY OF THE INVENTION

The optical unit according to the present invention comprises a light source unit emitting parallel light, a light-receiving element array, and a prism rendering emitted light from the light source unit incident on a specimen placement section and introducing totally reflected light from the specimen placement section into the light-receiving element array. The prism has an entrance surface rendering the parallel light emitted from the light source unit incident on the prism, a curved reflecting surface which reflects light passing through the entrance surface and incident on the prism toward its focal position, the specimen placement section of a planar shape provided at a position including the focal position of the curved reflecting surface, and an exit surface making light totally reflected at the focal position of the curved reflecting surface in the specimen placement section emerge into the outside of the prism.

In the optical unit of the present invention, it is desirable that the prism is constructed of a transparent member in which the curved reflecting surface is parabolic and the whole is configured into a nearly semicylindrical shape; the entrance surface, the specimen placement section, and the exit surface are provided on an identical plane passing through the focal position of the parabolic reflecting surface and perpendicular to an axis of symmetry and the entrance surface and the exit surface are arranged with the specimen placement section midway between them; the light source unit is located so that the parallel light emitted therefrom is incident perpendicularly on the entrance surface; individual light-receiving elements of the light-receiving element array are arranged in a one-dimensional direction so that light emerging perpendicularly from the exit surface is received perpendicularly by light-receiving surfaces; the parabolic reflecting surface has a first reflecting region which reflects the parallel light incident on the prism through the entrance surface to convert the light into incident light of continuous incident angles in a preset range including an angle of total reflection and renders the light incident on the focal position of the parabolic reflecting surface and a second reflecting region which reflects the light of continuous incident angles in the preset range, totally reflected at the focal position of the parabolic reflecting surface in the specimen placement section, to convert the light into parallel light and makes the light emerge perpendicularly from the exit surface into the outside of the prism.

In the optical unit of the present invention, it is desirable that the prism is constructed of a transparent member in which the curved reflecting surface is parabolic and the whole is configured into a rotationally symmetrical shape, with an axis of symmetry of the parabolic reflecting surface as a center; the entrance surface, the specimen placement section, and the exit surface are provided on an identical plane passing through the focal position of the parabolic reflecting surface and perpendicular to the axis of symmetry and the entrance surface and the exit surface are arranged with the specimen placement section midway between them; the light source unit is located so that the parallel light emitted therefrom is incident perpendicularly on the entrance surface; individual light-receiving elements of the light-receiving element array are arranged in a two-dimensional direction so that light emerging perpendicularly from the exit surface is received perpendicularly by light-receiving surfaces; the parabolic reflecting surface has a first reflecting region which reflects the parallel light incident on the prism through the entrance surface to convert the light into incident light of continuous incident angles in a preset range including an angle of total reflection and renders the light incident on the focal position of the parabolic reflecting surface and a second reflecting region which reflects the light of continuous incident angles in the preset range, totally reflected at the focal position of the parabolic reflecting surface in the specimen placement section, to convert the light into parallel light and makes the light emerge perpendicularly from the exit surface into the outside of the prism.

In the optical unit of the present invention, it is desirable that the prism includes a first sector-plate-shaped prism section, a second sector-plate-shaped prism section, and a third sector-plate-shaped prism section; the first sector-plate-shaped prism section has the entrance surface, a divergent light converting means converting the parallel light incident on the prism through the entrance surface into a sector-shaped divergent light, and a first arcuate reflecting surface deflecting the divergent light converted through the divergent light converting means; the first arcuate reflecting surface is inclined at 135 degrees with respect to the entrance surface; the divergent light converting means includes a reflecting surface which is perpendicular to the entrance surface at a top angle part of the first sector-plate-shaped prism section and provides a reflecting film to a conical hole whose top faces the entrance surface side; the second sector-plate-shaped prism section has a part of the specimen placement section and a second arcuate reflecting surface which constitutes the curved reflecting surface so that the light converted into the divergent light through the divergent light converting means in the first sector-plate-shaped prism section and deflected by the first arcuate reflecting surface is converted into a sector-shaped convergent light and is rendered incident on a focal position of the second arcuate reflecting surface and is identical in maximum diameter and top angle part with the first sector-plate-shaped prism section; the second arcuate reflecting surface is inclined at 45 degrees with respect to a sector surface with the maximum diameter in the second sector-plate-shaped prism section; the third sector-plate-shaped prism section has a remaining part of the specimen placement section and a third arcuate optical surface which constitutes the exit surface so that the sector-shaped divergent light converted by undergoing total reflection at the focal position of the second arcuate reflecting surface in the specimen placement section is made to emerge perpendicularly into the outside of the prism and is identical in maximum diameter and top angle part with the second sector-plate-shaped prism section; the third arcuate optical surface makes an angle of 90 degrees with the sector surface having the maximum diameter in the third sector-plate-shaped prism section; the first sector-plate-shaped prism section, the second sector-plate-shaped prism section, and the third sector-plate-shaped prism section are constructed of identical media; the first sector-plate-shaped prism section and the second sector-plate-shaped prism section are such that sector surfaces with the maximum diameters are cemented to each other; the second sector-plate-shaped prism section and the third sector-plate-shaped prism section are cemented to each other so that sector surfaces having the specimen placement section in common are practically flush with each other; the light source unit is placed perpendicular to the entrance surface of the first sector-plate-shaped prism section at a position where emitted parallel light is rendered incident on the conical reflecting surface in the first sector-plate-shaped prism section; and individual elements of the light-receiving element array are arranged to receive almost perpendicularly light emerging from the third arcuate optical surface in the third sector-plate-shaped prism section.

In the optical unit of the present invention, it is desirable that a metal film is evaporated on the specimen placement section.

These and other features and advantages of the present invention will become apparent from the following detailed description of the preferred embodiments when taken in conjunction with the accompanying drawings.

DETAILED DESCRIPTION OF THE PREFERRED EMBODIMENTS

Before undertaking the description of the embodiments, the fundamental structure and function of the optical unit will be outlined.

Figure 2:
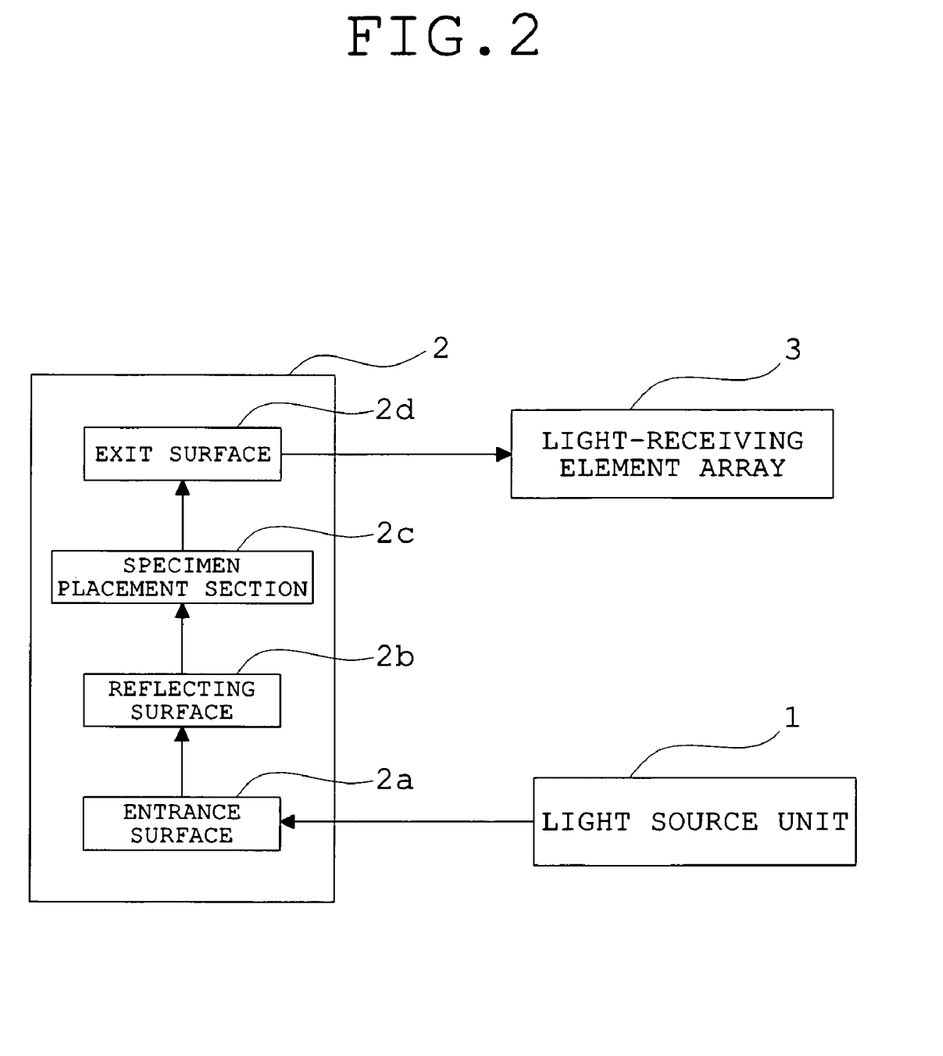
FIG. 2 is a block diagram showing conceptually a fundamental structure of the optical unit of the present invention.

FIG. 2 shows the fundamental structure of the optical unit. The optical unit is constructed to have a light source unit 1, a prism 2, and a light-receiving element array 3. The light source unit 1 is located at a position opposite to an entrance surface 2a of the prism 2. Also, a specific structure of the prism 2 will be described later. The light source unit 1 is constructed to emit parallel light. Any structure in which the parallel light can be emitted, for example, a structure combining a light source with a collimate lens or a structure combining them with a fiber, is satisfactory.

The light-receiving element array 3 is located at a position opposite to an exit surface 2d of the prism 2. Each element of the light-receiving element array 3 is placed along one direction. Here, the preset convergent light is incident on a specimen placement section 2c. Each ray of the preset convergent light is such that its incident angle is gradually changed. Each element of the light-receiving element array 3 is placed in a direction corresponding to the change of the incident angle. Also, a position where incident light is converged is also the focal position of a curved reflecting surface 2b. Each of the specimen displacing section 2c and the curved reflecting surface 2b is a part of the prism 2. Also, the direction of the arrangement of elements in the light-receiving elements array 3 is also the one along a virtual plane connecting the center of a beam of parallel light with the focal position of the curve reflecting surface 2b. In the optical unit, the incident angle is detected in accordance with a change of the intensity of received reflected light. A position where the change of the intensity of reflected light is brought about can be detected from the position of the light-receiving element. Thus, the light source unit 1 and the light-receiving element array 3 are adjusted so that such detection can be made.

The prism 2 is constructed so that the parallel light emitted from the light source unit 1 is rendered incident on the specimen placement section 2c and totally reflected light form the specimen placement section 2c is introduced into the light-receiving element array 3. Specifically, the prism 2 has the entrance surface 2a, the curved reflecting surface 2b, the planar specimen placement section 2c, and the exit surface 2d.

The entrance surface 2a is constructed so that the parallel light emitted from the light source unit 1 is rendered incident on the prism 2. In this case, it is desirable that the entrance surface 2a is flat and the parallel light is incident perpendicularly on the entrance surface 2a.

The curved reflecting surface 2b is constructed so that the parallel light transmitted through the entrance surface 2a to enter the prism 2 is reflected toward its focal position (not shown in the figure).

The planar specimen placement section 2c is provided at a position opposite to the curved reflecting surface 2b and containing the focal position of the curved reflecting surface 2b.

The exit surface 2d is constructed so that light totally reflected by the specimen placement section 2c is made to emerge into the outside of the prism 2. At this time, the totally reflected light becomes divergent light. It is thus desirable that the exit surface 2d is such that the normal line of the surface is perpendicular to each ray. Also, more specifically, the position where total reflection is produced is the focal position of the curved reflecting surface 2b.

In the case where the reflecting surface is absent in the direction in which the totally reflected light travels, the divergent light reaches the exit surface 2d. Hence, the exit surface 2d is configured into a curved shape such that the normal line of the surface becomes perpendicular to each ray. The exit surface 2d is located on the curved reflecting surface 2b side, that is, to be opposite to the entrance surface 2a and the specimen placement section 2c.

On the other hand, a curved reflecting surface may be provided in the direction in which the totally reflected light travels. This curved reflecting surface may be independent of the curved reflecting surface 2b or may be a surface connected with the curved reflecting surface 2b (a surface extending the curved reflecting surface 2b). In this case, the totally reflected light is reflected by the curved reflecting surface. The light reflected by the curved reflecting surface changes to parallel light identical with incident light. The exit surface 2d is configured into a planar shape such that the normal line of the surface is perpendicular to each ray. The exit surface 2d is located on the entrance surface 2a side and the specimen placement section 2c side, that is, to be opposite to the curved reflecting surface 2b.

In the optical unit constructed as mentioned above, the parallel light emitted from the light source unit 1 is incident on the entrance surface 2a of the prism 2. The light transmitted through the entrance surface 2a to enter the prism 2 is reflected by the curved reflecting surface 2b and is converged. Whereby, the parallel light changes to the preset convergent light, which is incident on the focal position of the curved reflecting surface 2b. At the focal position of the curved reflecting surface 2b, the specimen placement section 2c is located. The specimen is thus irradiated with the preset convergent light. Of the preset convergent light, a ray of light incident at an incident angle exceeding the critical angle undergoes total reflection and emerges perpendicularly from the exit surface 2d into the outside of the prism 2. The light emerging from the exit surface 2d into the outside of the prism 2 is received by each light-receiving element of the light-receiving element array 3.

In the optical unit, as described above, the entrance surface 2a of the prism 2 renders the parallel light emitted from the light source unit 1 incident perpendicularly on the prism 2. Consequently, any of rays constituting the parallel light is retained in a parallel state. The reflecting surface 2b is configured into a curved shape. Whereby, in the parallel light incident on the reflecting surface 2b, all rays thereof are reflected toward the focal position. The light incident on the prism 2 is converted into the preset convergent light and is incident on the focal position of the curved reflecting surface 2b. In addition, the exit surface 2d makes the light totally reflected from the specimen placement section 2c (the focal position of the curved reflecting surface 2b) emerge perpendicularly. In this case, any of rays constituting the totally reflected light retains the angle of total reflection as the information of an emergence position.

Specifically, according to the optical unit, neither the incident light on the prism 2 nor the emergent light from the prism 2 is refracted. Moreover, the conversion into the preset convergent light is carried out by the curved reflecting surface 2b. According to the optical unit, therefore, aberration produced in the prism 2 can be kept to a minimum. In particular, when the curved shape of the reflecting surface 2b is parabolic, no aberration is caused.

In this way, all the individual rays constituting the parallel light emitted from the light source unit 1 are converted into rays constituting the preset convergent light. In addition, since the prism 2 is favorably corrected for aberration (or is free of aberration), the preset convergent light is incident on the specimen placement section 2c (the focal position of the curved reflecting surface 2b) without causing positional and angular shifts. The divergent light totally reflected at the specimen placement section 2c (the focal position of the curved reflecting surface 2b) is received by corresponding light-receiving elements in the light-receiving element array 3 without causing positional and angular shifts.

The optical unit mentioned above can be utilized for the specimen analyzer, for instance. In the specimen analyzer, the specimen is placed on the specimen placement section 2c of the optical unit. The focal position of the curved reflecting surface 2b is irradiated with the preset convergent light, and reflected light obtained by total reflection is received by the light-receiving element array 3. In the light-receiving element array 3, a light intensity distribution is obtained by light-receiving elements located to correspond to incident angles. By analyzing the light intensity distribution, the incident angle corresponding to the critical angle can be found with a high degree of accuracy. From this incident angle, various physical properties of the specimen can be specified.

In the optical unit, a metal film is evaporated on the specimen placement section $2c$, for example, in such a way that the specimen placement section $2c$ is coated with a thin meal film or fine metal particles. By doing so, the incident angle where the intensity of reflected light is abruptly changed by surface plasmon resonance can be found with a high degree of accuracy. In addition, various physical properties of the specimen can be specified from this incident angle.

According to the optical unit, as discussed above, the same point of an object to be examined can be irradiated with light allowing some latitude in the incident angle without yielding aberration. Consequently, in order to detect the incident angle of the ray with a high degree of accuracy, it is not necessary to use an aberration correcting lens or an aspherical lens. Moreover, by saving a layout space, a compact design can be attained and further the cost can be reduced.

First Embodiment

Figure 3A:
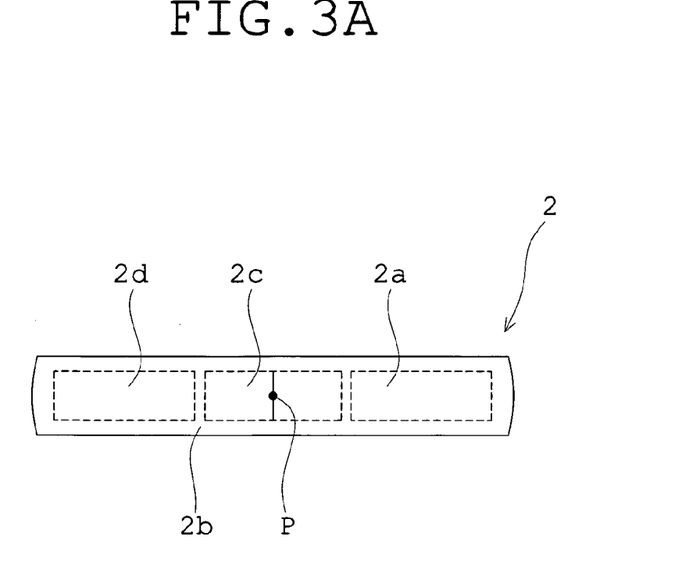
FIGS. 3A and 3B are illustrations of the optical unit according to a first embodiment in the present invention, which are a view where the optical unit is viewed from the direction of the optical axis and a sectional view showing schematically the entire structure of the optical unit developed along the optical axis, respectively.
Figure 3B:
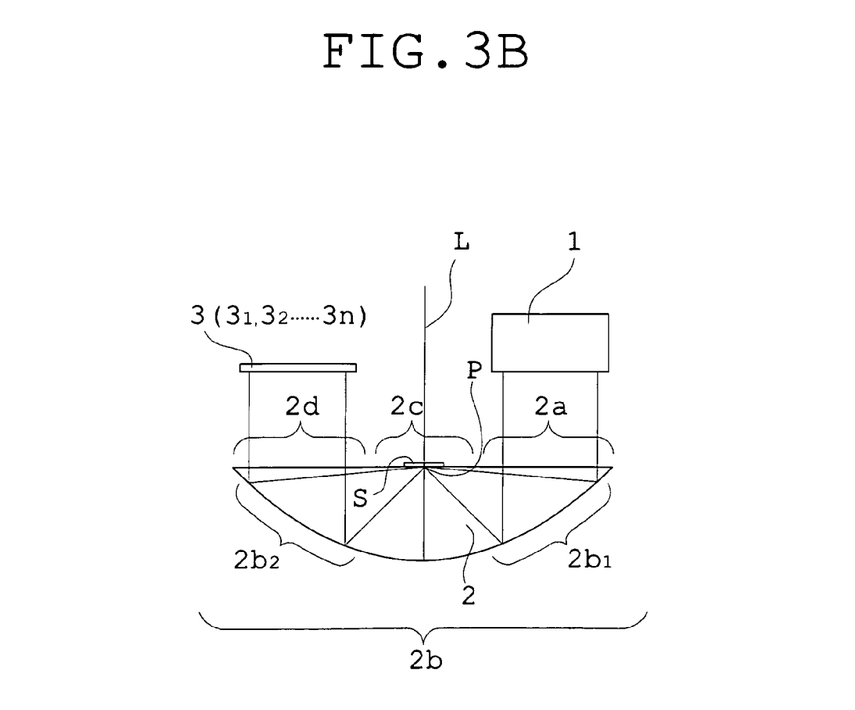
Figure 4:
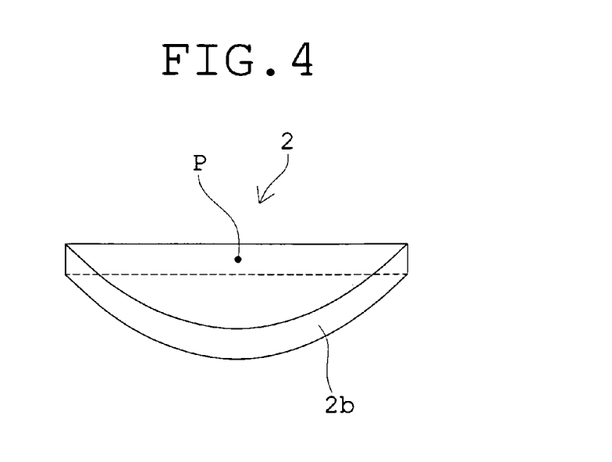
FIG. 4 is a perspective view showing the appearance of a prism used in the optical unit for specimen analysis in FIGS. 3A and 3B.

FIGS. 3A and 3B show the optical unit according to the first embodiment. FIG. 4 show the appearance of the prism used in the optical unit of FIG. 3B. Also, in FIG. 3B, reference symbol S represents a specimen.

In the optical unit of this embodiment, the prism 2 is constructed of a transparent member in which the curved reflecting surface $2b$ is parabolic and the whole is configured into a nearly semicylindrical shape.

The prism 2 has the entrance surface $2a$, the parabolic reflecting surface $2b$, and the exit surface $2d$. The parabolic reflecting surface $2b$ is a part of a paraboloid. An axis of symmetry L is a rotationally symmetrical axis (a center axis) of the paraboloid. The entrance surface $2a$, the specimen placement section $2c$, and the exit surface $2d$ are provided on the same plane. This plane contains a focal position P of the parabolic reflecting surface $2b$ and is perpendicular to the axis of symmetry L. The entrance surface $2a$ and the exit surface $2d$ are arranged with the specimen placement section $2c$ midway between them.

The light source unit 1 is located so that the parallel light emitted therefrom is rendered incident perpendicularly on the entrance surface $2a$.

Individual light-receiving elements $3_1, 3_2, \ldots,$ and $3_n$ of the light-receiving element array 3 are arranged in one-dimensional direction so that light (individual rays constituting the parallel light) emerging perpendicularly from the exit surface $2d$ is received perpendicularly by light-receiving surfaces.

The parabolic reflecting surface $2b$ has a first reflecting region $2b_1$ and a second reflecting region $2b_2$. The first reflecting region $2b_1$ reflects the parallel light incident on the prism 2 through the entrance surface $2a$ to convert the light into the preset convergent light, which is rendered incident on the focal point P of the parabolic reflecting surface $2b$.

The second reflecting region $2b_2$ reflects the preset convergent light totally reflected by the focal point P of the parabolic reflecting surface $2b$ in the specimen placement section $2c$ to convert the light into parallel light, which is made to emerge perpendicularly from the exit surface $2d$ into the outside of the prism 2.

Other features are the same as in FIG. 2.

In the optical unit of the first embodiment constructed as mentioned above, the parallel light emitted from the light source unit 1 is incident perpendicularly on the entrance surface $2a$ of the prism 2. Here, the entire contour of the parallel light, for example, as indicated by broken lines in FIG. 3A, has a nearly rectangular shape. The parallel light transmitted through the entrance surface $2a$ to enter the prism is reflected by the first reflecting region $2b_1$ in the parabolic reflecting surface $2b$. Whereby, the parallel light is converted into the preset convergent light and is incident on the specimen placement section $2c$, more specifically, the focal position P of the parabolic reflecting surface $2b$.

As mentioned above, the parabolic reflecting surface $2b$ constitutes a part of the paraboloid. However, the reflecting surface $2b$ has the parabolic shape only in a longitudinal direction. This longitudinal direction refers to the one in which the entrance surface $2a$, the specimen placement section $2c$, and the exit surface $2d$ are arranged. In terms of nearly rectangular parallel light, the longitudinal direction is the one of the major axis of a rectangle. On the other hand, the parabolic reflecting surface $2b$ has no optical power in a transverse direction (a direction perpendicular to the longitudinal direction). Thus, the parallel light reflected by the parabolic reflecting surface $2b$ changes to convergent light whose width is kept constantly in the transverse direction. Consequently, strictly speaking, light collected in the specimen placement section $2c$ is condensed on a line including the focal point P.

Of light incident on the specimen placement section $2c$ (the focal position P of the parabolic reflecting surface $2b$), light incident at the incident angle exceeding the critical angle undergoes total reflection. The totally reflected light is directed toward the second reflecting region $2b_2$ in the parabolic reflecting surface $2b$. This reflected light is reflected by the second reflecting region $2b_2$ and is converted into parallel light. The reflected light converted into the parallel light emerges perpendicularly from the planar exit surface $2d$ into the outside of the prism 2. The light emerging from the exit surface $2d$ into the outside of the prism 2 is received by individual light-receiving elements of the light-receiving element array 3. Thus, in consideration of a parallel light beam (a nearly rectangular parallel light beam) having a limited width in a direction perpendicular to the plane of the page in FIG. 3B, the conversion into a parallel beam, a convergent beam, a divergent beam, and a parallel beam in this order, such as that shown in FIG. 3B, is carried out in a plane parallel to the plane of the page.

In the optical unit of the first embodiment, as mentioned above, the entrance surface $2a$ of the prism 2 renders the parallel light emitted from the light source unit 1 incident perpendicularly on the prism 2. Hence, any of rays constituting the parallel light is retained in a parallel state. The first reflecting region $2b_1$ in the reflecting surface $2b$ has the function of reflecting all the rays (the individual rays of the parallel light incident thereon) toward the focal position P of the reflecting surface $2b$. The parallel light incident on the prism 2 is therefore converted into the preset convergent light to enter the focal position P of the reflecting surface $2b$. At this time, the parallel light incident on the prism 2 does not pass through any medium other than that of the prism 2.

The second reflecting region $2b_2$ in the reflecting surface $2b$ has the function of reflecting all the rays incident thereon from the focal position P of the reflecting surface $2b$ to convert the rays into parallel light. Consequently, the light totally reflected at the focal point P of the reflecting surface $2b$ is converted into parallel light and is incident perpendicularly on the exit surface $2d$ of the prism 2. Also, the totally reflected light does not pass through any medium other than that of the prism 2. The exit surface 2d of the prism 2 makes the parallel light incident thereon emerge into the outside of the prism 2. Hence, any of rays constituting the parallel light is retained in a parallel state. At this time, any of individual rays of the parallel light emerging from the exit surface 2d retains the angle of total reflection as the information of an emergence position.

Specifically, according to the optical unit of the first embodiment, neither the incident light on the prism 2 nor the emergent light from the prism 2 is refracted. Moreover, the conversion into the preset convergent light and the conversion of the light totally reflected at the focal position P into parallel light are carried out by the parabolic reflecting surface 2b inside the prism 2 of the same medium. According to the optical unit of the embodiment, therefore, no aberration is caused in the prism 2.

In this way, all the individual rays constituting the parallel light emitted from the light source unit 1 are converted into rays constituting the preset convergent light. In addition, since no aberration is produced in the prism 2, the preset convergent light is incident on the specimen placement section 2c (the focal position P of the parabolic reflecting surface 2b) without causing positional and angular shifts. The divergent light totally reflected at the focal position P of the parabolic reflecting surface 2b is converted into parallel light without causing positional and angular shifts. This parallel light is received by corresponding light-receiving elements in the light-receiving element array 3.

The optical unit of the embodiment constructed in this way can be utilized for the specimen analyzer, for instance. In the specimen analyzer, the specimen is placed on the specimen placement section 2c of the optical unit of the first embodiment. The focal position P of the parabolic reflecting surface 2b is irradiated with the preset convergent light, and reflected light obtained by total reflection is received by the light-receiving element array 3. In the light-receiving element array 3, a light intensity distribution is obtained by light-receiving elements located to correspond to incident angles. By analyzing the light intensity distribution, the incident angle corresponding to the critical angle can be found with a high degree of accuracy. From this incident angle, various physical properties of the specimen can be specified.

In the optical unit of the first embodiment, a metal film is evaporated on the specimen placement section 2c, for example, in such a way that the specimen placement section 2c is coated with a thin meal film or fine metal particles. By doing so, the incident angle where the intensity of reflected light is abruptly changed by surface plasmon resonance can be found with a high degree of accuracy. In addition, various physical properties of the specimen can be specified from this incident angle.

According to the optical unit of the first embodiment, as discussed above, the same point of an object to be examined can be irradiated with light allowing some latitude in the incident angle without yielding aberration. Consequently, in order to detect the incident angle of the ray with a high degree of accuracy, it is not necessary to use an aberration correcting lens or an aspherical lens. Moreover, by saving a layout space, a compact design can be attained and further the cost can be reduced.

Figure 5A:
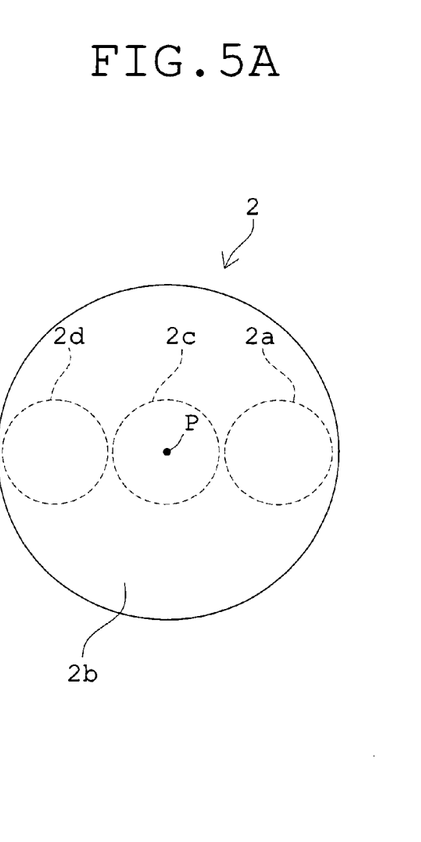
FIGS. 5A and 5B are explanatory views illustrating a modified example of the optical unit according to the first embodiment in the present invention, which are a view where the optical unit is viewed from the direction of the optical axis and a sectional view showing schematically the entire structure of the optical unit developed along the optical axis, respectively.
Figure 5B:
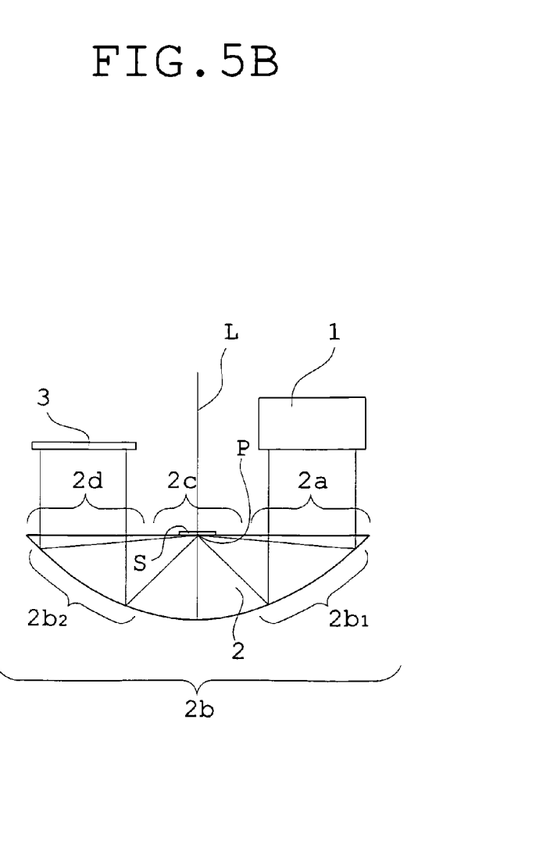

The modified example of the optical unit is shown in FIGS. 5A and 5B. In FIGS. 3A and 3B and FIG. 4, the prism 2 is constructed of a transparent member in which the curved reflecting surface 2b is parabolic and the whole is configured into a nearly semicylindrical shape. In contrast to this, the prism 2, as shown in FIGS. 5A and 5B, may be constructed of a transparent member in which the curved reflecting surface 2b is parabolic and the whole is configured into a rotationally symmetrical shape, with the axis of symmetry L of the parabolic reflecting surface 2b as a center. In this case, a parallel beam of light is collected at the focal point P.

In FIGS. 3A and 3B and FIG. 4, the incident light is linearly collected on the specimen placement section 2c. Hence, in this structure, the measurement is made in a linear region on the specimen. In the rotationally symmetrical type parabolic surface shown in FIGS. 5A and 5B, by contrast, the light is converged on the specimen placement section 2c. Consequently, the measurement of a minute region of only one point on the specimen becomes possible.

Second Embodiment

Figure 6A:
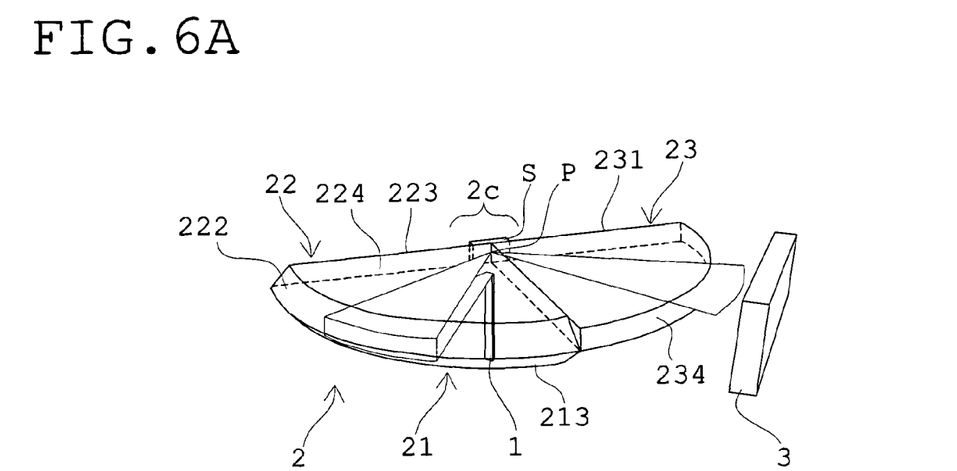
FIGS. 6A, 6B, and 6C are explanatory views illustrating schematically the entire structure of the optical unit according to a second embodiment in the present invention, which are a perspective view, a sectional view developed along the optical axis, and a side view from the opposite side of the specimen placement section, respectively.
Figure 6B:
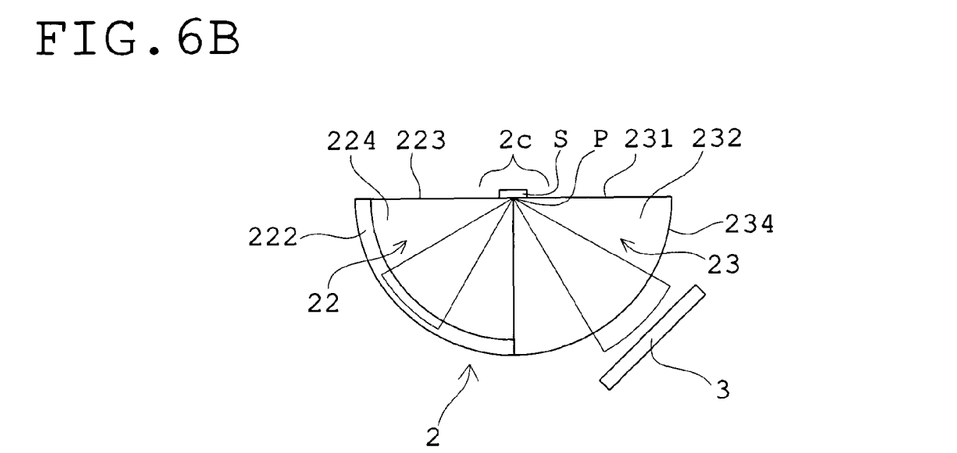
Figure 6C:
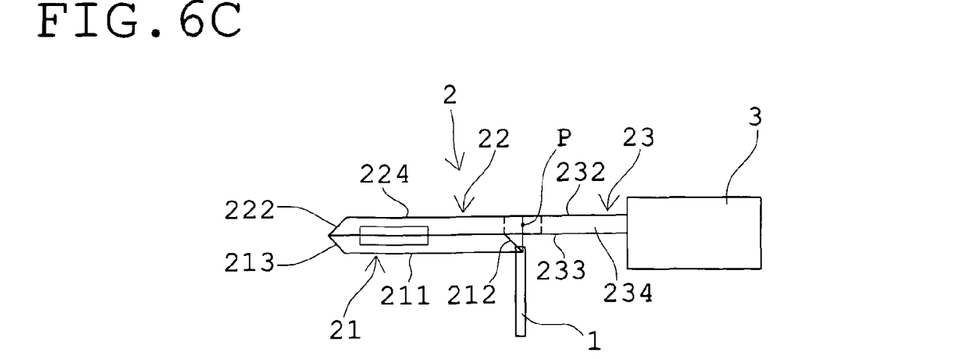
Figure 7A:
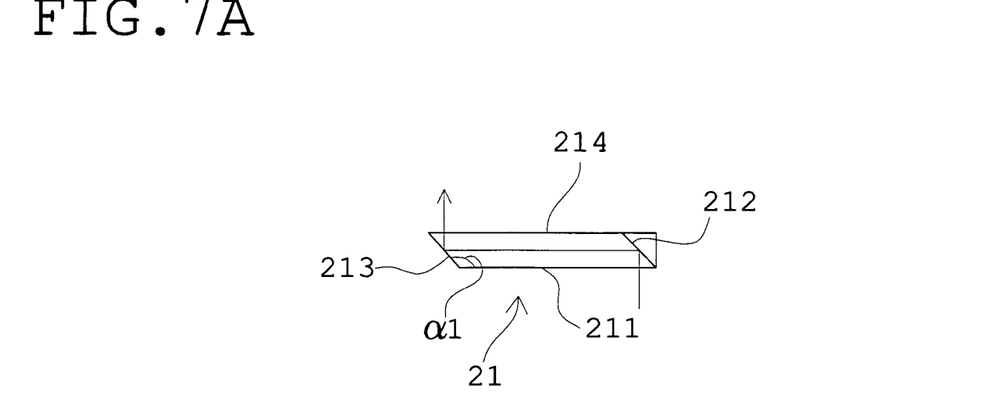
FIGS. 7A, 7B, and 7C are side views illustrating schematically various components of the prism in the optical unit of FIGS. 6A, 6B, and 6C, which show the first sector-plate-shaped prism section, the second sector-plate-shaped prism section, and the third sector-plate-shaped prism section, respectively.
Figure 7B:
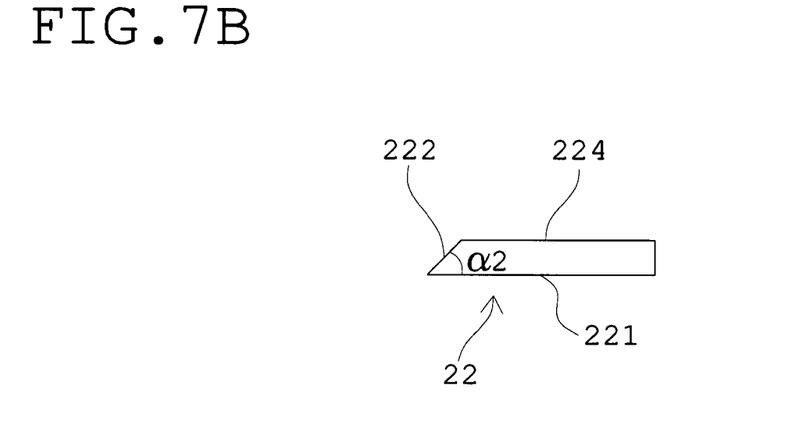
Figure 7C:
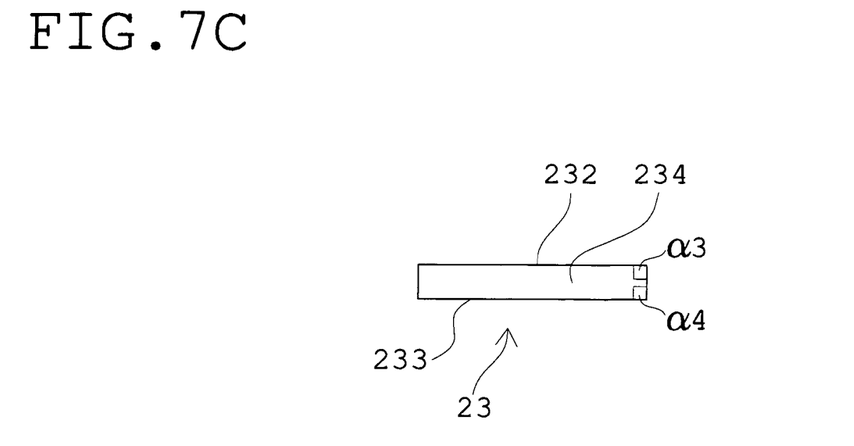

FIGS. 6A, 6B, and 6C show schematically the entire structure of the optical unit according to a second embodiment in the present invention. FIGS. 7A, 7B, and 7C show schematically various components of the prism in the optical unit of FIGS. 6A, 6B, and 6C. Also, in FIGS. 6A and 6B, reference symbol S denotes the specimen.

In the optical unit of the second embodiment, the prism 2, as illustrated in FIGS. 6A-6C, includes a first sector-plate-shaped prism section 21, a second sector-plate-shaped prism section 22, and a third sector-plate-shaped prism section 23.

The first sector-plate-shaped section 21 has a sector surface 211 constituting the entrance surface 2a, a divergent light converting means 212, a first arcuate reflecting surface 213, and a sector surface 214.

The divergent light converting means 212 is constructed with a conical hole and a reflecting surface that a reflecting film is deposited on a conical surface. The conical hole is configured so that its center axis passes through the top angle part of the first sector-plate-shaped prism section 21 (namely, the focal position P of the first arcuate reflecting surface 213 described later). The conical hole is further configured so that its center axis is perpendicular to the entrance surface 2a (the sector surface 211) and its top faces the entrance surface 2a (the sector surface 211) side. Hence, the reflecting surface of the divergent light converting means 212 is opposite to the first arcuate reflecting surface 213.

The first arcuate reflecting surface 213 has the shape that a part of a conical surface is cut like a strip. The reflecting surface 213 is arcuate along the longitudinal direction and thus has the optical power in this direction. On the other hand, in a direction perpendicular to the longitudinal direction (namely, in a direction of the generatrix of the cone), the reflecting surface 213 has no optical power. The reflecting surface 213 is provided (configured) so that an angle $\alpha 1$ made with the entrance surface 2a (the sector surface 211) is 135 degrees.

In the first sector-plate-shaped prism section 21, parallel light from the light source unit 1 is incident on the prism 2 through the entrance surface 2a (the sector surface 211). The parallel light incident on the prism 2 is converted into a sector-shaped divergent light, with the focal position P of the first arcuate reflecting surface 213 as a center, by the divergent light converging means 212. The first arcuate reflecting surface 213 deflects the sector-shaped divergent light to the second sector-plate-shaped prism section 22 side.

The second sector-plate-shaped prism section 22 has a sector surface 221, a second arcuate reflecting surface 222, a flat surface 223 having a part of the specimen placement section 2c, and a sector surface 224.

The second arcuate reflecting surface 222 is a curved reflecting surface and specifically, has the same shape as the first arcuate reflecting surface 213. The second arcuate reflecting surface 222 is provided so that an angle α2 made with the sector surface 221 is 45 degrees. As seem from the figures, the second arcuate reflecting surface 222 is provided to be opposite to the first arcuate reflecting surface 213.

The flat surface 223 is provided to be opposite to the second arcuate reflecting surface 222. This flat surface 223 is the one containing the focal position P of the second arcuate reflecting surface 222. The flat surface 223 also contains a part of the specimen placement section 2c. In the specimen placement section 2c, its position is set so that the focal position P of the second arcuate reflecting surface 222 is contained.

The maximum diameter and top angle part of the second sector-plate-shaped prism section 22 are the same as in the first sector-plate-shaped prism section 21. The sector surface 221 has the maximum diameter in the second sector-plate-shaped prism section 22.

In the second sector-plate-shaped prism section 22, the light deflected by the first arcuate reflecting surface 213 is incident on the second arcuate reflecting surface 222. This light is converted into a sector-shaped convergent light by the second arcuate reflecting surface 222 and reaches the focal position P. At the focal point P, as mentioned above, the specimen placement section 2c is located. The convergent light is thus incident on the specimen placement section 2c.

The third sector-plate-shaped prism section 23 has a flat surface 231 having a remaining part of the specimen placement section 2c, a sector surface 232, a sector surface 233, and a third arcuate optical surface 234.

The third arcuate optical surface 234 is the exit surface 2d, and specifically, has the shape that a part of the cylindrical surface is cut like a strip. The optical surface 234 is arcuate along the longitudinal direction and thus has the optical power in this direction. On the other hand, in a direction perpendicular to the longitudinal direction (namely, in a direction of the generatrix of the cylinder), the optical surface 234 has no optical power. The third arcuate optical surface 234 is provided so that angles α3 and α4 made with the sector surfaces 232 and 233, respectively, is 90 degrees.

The flat surface 231 is provided to be opposite to the third arcuate optical surface 234. This flat surface 231 is the one containing the focal position P of the second arcuate reflecting surface 222. The flat surface 231 also contains a part of the specimen placement section 2c. In this embodiment, the flat surfaces 223 and 231 constitute a continuous plane and both come in contact with each other at the focal point P of the second arcuate reflecting surface 222.

The maximum diameter and top angle part of the third sector-plate-shaped prism section 23 are the same as in the second sector-plate-shaped prism section 22. Each of the sector surfaces 232 and 233 has the maximum diameter in the third sector-plate-shaped prism section 23.

In the third sector-plate-shaped prism section 23, a part of light, of the convergent light incident on the specimen placement section 2c, changes to a sector-shaped divergent light to enter the third arcuate optical surface 234. The light incident on the third arcuate optical surface 234 makes rays constituting the sector-shaped convergent light emerge perpendicularly into the outside of the prism.

The first sector-plate-shaped prism section 21, the second sector-plate-shaped prism section 22, and the third sector-plate-shaped prism section 23 are constructed of identical media.

The first sector-plate-shaped prism section 21 and the second sector-plate-shaped prism section 22 are such that the sector surfaces 214 and 221 with the maximum diameters are cemented to each other. The second sector-plate-shaped prism section 22 and the third sector-plate-shaped prism section 23 are cemented to each other so that the flat surfaces 223 and 231 having the specimen placement section 2c, as well as the sector surfaces 224 and 232 and the sector surfaces 221 and 233, are practically flush with each other.

The light source unit 1 is placed perpendicular to the entrance surface 211 of the first sector-plate-shaped prism section 21 at a position where emitted parallel light is rendered incident on the conical reflecting surface 212 in the first sector-plate-shaped prism section 21.

Individual elements of the light-receiving element array 3 are arranged to receive almost perpendicularly light emerging from the third arcuate optical surface 234 in the third sector-plate-shaped prism section 23.

Other features are the same as those shown in FIG. 2.

In the optical unit of the second embodiment constructed in this way, the parallel light emitted from the light source unit 1 is incident perpendicularly on the entrance surface 2a (the sector surface 211) of the first sector-plate-shaped prism section 21. The parallel light transmitted through the entrance surface 2a (the sector surface 211) and incident on the prism section 21 is incident on the conical reflecting surface that is the divergent light converting means 212. The parallel light incident on the conical reflecting surface 212 is reflected by the conical reflecting surface 212. Whereby, the parallel light is converted into a sector-shaped divergent light, which is incident on the first arcuate reflecting surface 213. The sector-shaped divergent light incident on the first arcuate reflecting surface 213 is reflected by the first arcuate reflecting surface 213. Whereby, the sector-shaped divergent light is deflected to the second sector-plate-shaped prism section 22 side and is perpendicularly transmitted through the sector surfaces 214 and 221 to enter the second arcuate reflecting surface 222. The light incident on the second arcuate reflecting surface 222 is reflected by the second arcuate reflecting surface 222. Whereby, the sector-shaped divergent light is converted into a sector-shaped convergent light to enter the specimen placement section 2c (the focal position P of the second arcuate reflecting surface 222). Also, in the second embodiment, this sector-shaped convergent light corresponds to the preset convergent light.

Of the light incident on the specimen placement section 2c (the focal position P of the second arcuate reflecting surface 222), light incident at an incident angle exceeding the critical angle undergoes total reflection. The reflected light undergoing the total reflection is converted into a sector-shaped divergent light, which is incident on the third sector-plate-shaped prism section 23. The sector-shaped divergent light incident on the third sector-plate-shaped prism section 23 emerges perpendicularly from the exit surface 2d (the third arcuate optical surface 234) into the outside of the third sector-plate-shaped prism section 23. The light emerging from the exit surface 2d of the third sector-plate-shaped prism section 23 (the third arcuate optical surface 234) into the outside of the third sector-plate-shaped prism section 23 is received by the individual light-receiving elements of the light-receiving element array 3.

In the optical unit of the second embodiment, as discussed above, the entrance surface 2a of the first sector-plate-shaped prism section 21 renders the parallel light emitted from the light source unit 1 incident perpendicularly on the first sector-plate-shaped prism section 21. Hence, any of rays constituting the parallel light is retained in a parallel state. The divergent light converting means 212 is provided at the top angle part of the first sector-plate-shaped prism section 21 (the focal position P of the first arcuate reflecting surface 213). Whereby, the parallel light incident on the first sector-plateshaped prism section 21 is converted into a sector-shaped divergent light. This sector-shaped divergent light is the one, with the focal position P of the first arcuate reflecting surface 213 as a center. Hence, the sector-shaped divergent light can be rendered incident on the first arcuate reflecting surface 213 at an equal incident angle. In the first arcuate reflecting surface 213, the inclination angle α1 made with the entrance surface 2a (the sector surface 211) is 135 degrees and thus the sector-shaped divergent light can be deflected in a perpendicular direction. Here, the deflected light is perpendicularly transmitted through the sector surfaces 214 and 221. Hence, any of rays of the deflected light is retained in a perpendicular state to enter the second arcuate reflecting surface 222.

The second arcuate reflecting surface 222 has the function of reflecting the incident light toward the focal position P of the second arcuate reflecting surface 222. Thus, the divergent light incident on the second arcuate reflecting surface 222 is such that all the rays are reflected toward the focal position P. In the second arcuate reflecting surface 222, the inclination angle α2 made with the sector surface 221 is 45 degrees. Therefore, the light incident perpendicularly on the second sector-plate-shaped prism section 22 from the sector surface 221 is reflected toward the focal position P in a horizontal direction. In addition, the first sector-plate-shaped prism section 21 and the second sector-plate-shaped prism section 22 are constructed of identical media. The sector surfaces 214 and 221 having the maximum diameters are cemented to each other. Consequently, the parallel light incident on the first sector-plate-shaped prism section 21 is incident on the second sector-plate-shaped prism section 22 without passing through any medium other than that of the prism 2. The incident parallel light is converted into the preset converting light through the second arcuate reflecting surface 222 of the second sector-plate-shaped prism section 22. This preset converging light is incident on the focal position P of the second arcuate reflecting surface 222.

The third sector-plate-shaped prism section 23 is constructed of the medium identical with the second sector-plate-shaped prism section 22. The flat surfaces 223 and 231 having the specimen placement section 2c are cemented to be practically flush with each other. Likewise, the sector surfaces 224 and 232, as well as the sector surfaces 221 and 233, are cemented to be practically flush with each other. Moreover, the third sector-plate-shaped prism section 23 has the third arcuate optical surface 234 as the exit surface 2d. As described above, the preset convergent light incident on the focal position P of the second arcuate reflecting surface 222 undergoes total reflection here and thereby is converted into a sector-shaped divergent light. This sector-shaped divergent light emerges toward outside. The third arcuate optical surface 234 is configured into an arcuate shape so that the divergent light is capable of emerging perpendicularly. Consequently, the divergent light (the light undergoing total reflection at the focal position P of the second arcuate reflecting surface 222) emerges perpendicularly from the exit surface 2d of the third sector-plate-shaped prism section 23 into the outside of the prism 2. At this time, the divergent light does not pass through any medium other than that of the prism 2. Hence, any of rays constituting the divergent light is retained in a traveling state. In this case, any of rays of the divergent light emerging from the exit surface 2d retains the angle of total reflection as the information of an emergence position.

Specifically, according to the optical unit of the second embodiment, neither the incident light on the first sector-plate-shaped prism section 21 nor the emergent light from the third sector-plate-shaped prism section 23 is refracted. Moreover, the conversion into the preset convergent light is carried out by the second arcuate reflecting surface 222 in the second sector-plate-shaped prism section 22. Here, the second sector-plate-shaped prism section 22 is constructed of the medium identical with the first sector-plate-shaped prism section 21 and the third sector-plate-shaped prism section 23. According to the optical unit of the second embodiment, therefore, no aberration is produced in the prism 2.

In this way, all the rays constituting the parallel light emitted from the light source unit 1 are converted into rays constituting the preset convergent light. In addition, since no aberration is produced in the prism 2, the preset convergent light is incident on the specimen placement section 2c (the focal position P of the second arcuate reflecting surface 222) without causing positional and angular shifts. The divergent light totally reflected at the focal position P of the second arcuate reflecting surface 222 is received by corresponding light-receiving elements in the light-receiving element array 3 without causing positional and angular shifts.

The optical unit of the embodiment constructed in this way can be utilized for the specimen analyzer, for instance. In the specimen analyzer, the specimen is placed on the specimen placement section 2c of the optical unit of the second embodiment. The focal position P of the second arcuate reflecting surface 222 is irradiated with the preset convergent light, and reflected light obtained by total reflection is received by the light-receiving element array 3. In the light-receiving element array 3, a light intensity distribution is obtained by light-receiving elements located to correspond to incident angles. By analyzing the light intensity distribution, the incident angle corresponding to the critical angle can be found with a high degree of accuracy. From this incident angle, various physical properties of the specimen can be specified.

In the optical unit of the second embodiment, a metal film is evaporated on the specimen placement section 2c, for example, in such a way that the specimen placement section 2c is coated with a thin meal film or fine metal particles. By doing so, the incident angle where the intensity of reflected light is abruptly changed by surface plasmon resonance can be found with a high degree of accuracy. In addition, various physical properties of the specimen can be specified from this incident angle.

According to the optical unit of the second embodiment, as discussed above, the same point of an object to be examined can be irradiated with light allowing some latitude in the incident angle without yielding aberration. Consequently, in order to detect the incident angle of the ray with a high degree of accuracy, it is not necessary to use an aberration correcting lens or an aspherical lens. Moreover, by saving a layout space, a compact design can be attained and further the cost can be reduced.

Furthermore, according to the optical unit of the second embodiment, since the parallel light emitted from the light source unit 1 and incident on the first sector-plate-shaped prism section 21 through the entrance surface 2a (the sector surface 211) is converted into the divergent light through the divergent light converting means 212, the same point of an object to be examined can be irradiated with light allowing some latitude in the incident angle without enlarging the emission section of the light source unit 1, and the light source unit can be made compact.

Also, in the optical unit of the second embodiment, it is desirable that an interface between the first sector-plate-shaped prism section 21 and the second sector-plate-shaped prism section 22 (namely, an interface between the sector surface 214 and the sector surface 221) is provided with a light-blocking member that has a slit on the optical path along which the light deflected by the first arcuate reflecting surface 213 is directed toward the second arcuate reflecting surface 222.

By doing so, stray light that does not follow a path from the divergent light converting means 212 to the first arcuate reflecting surface 213 in the first sector-plate-shaped prism section 21 can be blocked from incidence on the second sector-plate-shaped prism section 22. As a result, light-receiving accuracy in the light-receiving element array 3 becomes higher.

According to the present invention, the optical unit is obtained in which the structure is simple, the occurrence of aberration is kept to a minimum, and the incident angle of the ray can be detected with a high degree of accuracy.

The optical unit of the present invention is useful in the fields of medical treatment, medical science, and biology in which total reflection is utilized for analyzing the physical property of the specimen.

What is claimed is:

1. An optical unit comprising:
   a light source unit emitting parallel light;
   a light-receiving element array; and
   a prism rendering emitted light from the light source unit incident on a specimen placement section and introducing totally reflected light from the specimen placement section into the light-receiving element array,
   the prism having an entrance surface rendering the parallel light emitted from the light source unit incident on the prism, a curved reflecting surface which reflects light passing through the entrance surface and incident on the prism toward a focal position thereof, the specimen placement section of a planar shape provided at a position including the focal position of the curved reflecting surface, and an exit surface making light totally reflected at the focal position of the curved reflecting surface in the specimen placement section emerge into an outside of the prism.

2. An optical unit according to claim 1, wherein the prism is constructed of a transparent member in which the curved reflecting surface is parabolic and a whole is configured into a nearly semicylindrical shape; the entrance surface, the specimen placement section, and the exit surface are provided on an identical plane passing through the focal position of the parabolic reflecting surface and perpendicular to an axis of symmetry and the entrance surface and the exit surface are arranged with the specimen placement section midway between the entrance surface and the exit surface; the light source unit is located so that the parallel light emitted therefrom is rendered incident perpendicularly on the entrance surface; individual light-receiving elements of the light-receiving element array are arranged in a one-dimensional direction so that light emerging perpendicularly from the exit surface is received perpendicularly by light-receiving surfaces; the parabolic reflecting surface has a first reflecting region which reflects the parallel light incident on the prism through the entrance surface to convert the light into incident light of continuous incident angles in a preset range including the angle of total reflection and renders the light incident on the focal position of the parabolic reflecting surface, and a second reflecting region which reflects the light of continuous incident angles in the preset range, totally reflected at the focal position of the parabolic reflecting surface in the specimen placement section to convert the light into parallel light, and is made to emerge perpendicularly from the exit surface into the outside of the prism.

3. An optical unit according to claim 1, wherein the prism is constructed of a transparent member in which the curved reflecting surface is parabolic and a whole is configured into a rotationally symmetrical shape, with an axis of symmetry of the parabolic reflecting surface as a center; the entrance surface, the specimen placement section, and the exit surface are provided on an identical plane passing through the focal position of the parabolic reflecting surface and perpendicular to the axis of symmetry and the entrance surface and the exit surface are arranged with the specimen placement section midway between the entrance surface and the exit surface; the light source unit is located so that the parallel light emitted therefrom is incident perpendicularly on the entrance surface; individual light-receiving elements of the light-receiving element array are arranged in a two-dimensional direction so that light emerging perpendicularly from the exit surface is received perpendicularly by light-receiving surfaces; the parabolic reflecting surface has a first reflecting region which reflects the parallel light incident on the prism through the entrance surface to convert the light into incident light of continuous incident angles in a preset range including an angle of total reflection and renders the light incident on the focal position of the parabolic reflecting surface and a second reflecting region which reflects the light of continuous incident angles in the preset range, totally reflected at the focal position of the parabolic reflecting surface in the specimen placement section, to convert the light into parallel light and makes the light emerge perpendicularly from the exit surface into the outside of the prism.

4. An optical unit according to claim 1, wherein the prism includes a first sector-plate-shaped prism section, a second sector-plate-shaped prism section, and a third sector-plate-shaped prism section; the first sector-plate-shaped prism section has the entrance surface, a divergent light converting means converting the parallel light incident on the prism through the entrance surface into a sector-shaped divergent light, the divergent light converting means including a reflecting surface which is perpendicular to the entrance surface at a top angle part of the first sector-plate-shaped prism section and provides a reflecting film to a conical hole whose top faces an entrance surface side, and a first arcuate reflecting surface deflecting the divergent light converted through the divergent light converting means, the first arcuate reflecting surface being inclined at 135 degrees with respect to the entrance surface; the second sector-plate-shaped prism section is identical in maximum diameter and top angle part with the first sector-plate-shaped prism section and has a part of the specimen placement section and a second arcuate reflecting surface in which the light converted into the divergent light through the divergent light converting means in the first sector-plate-shaped prism section and deflected by the first arcuate reflecting surface is converted into a sector-shaped convergent light and is rendered incident on a focal position of the second arcuate reflecting surface, the second arcuate reflecting surface constituting the curved reflecting surface and being inclined at 45 degrees with respect to a sector surface with a maximum diameter in the second sector-plate-shaped prism section; the third sector-plate-shaped prism section is identical in maximum diameter and top angle part with the second sector-plate-shaped prism section and has a remaining part of the specimen placement section and a third arcuate optical surface which constitutes the exit surface so that the sector-shaped divergent light converted by undergoing total reflection at the focal position of the second arcuate reflecting surface in the specimen placement section is made to emerge perpendicularly into the outside of the prism, the third arcuate optical surface making an angle of 90 degrees with the sector surface having a maximum diameter in the third sector-plate-shaped prism section; the first sector-plate-shaped prism section, the second sector-plate-shaped prism section, and the third sector-plate-shaped prism section are constructed of identical media; the first sector-plate-shaped prism section and the second sector-plate-shaped prism section are such that sector surfaces with maximum diameters are cemented to each other; the second sector-plate-shaped prism section and the third sector-plate-shaped prism section are cemented to each other so that sector surfaces having the specimen placement section in common are practically flush with each other; the light source unit is placed perpendicular to the entrance surface of the first sector-plate-shaped prism section at a position where emitted parallel light is rendered incident on the conical reflecting surface in the first sector-plate-shaped prism section; and individual elements of the light-receiving element array are arranged to receive almost perpendicularly light emerging from the third arcuate optical surface in the third sector-plate-shaped prism section.

5. An optical unit according to claim 1, wherein a metal film is evaporated on the specimen placement section.

* * * * *